(12) United States Patent
Petersen

(10) Patent No.: US 9,994,553 B2
(45) Date of Patent: Jun. 12, 2018

(54) PROCESS FOR THE PURIFICATION OF THE AXL TYROSINE RECEPTOR KINASE INHIBITOR "R428"

(71) Applicant: BerGenBio AS, Bergen (NO)

(72) Inventor: Lene Raunkjaer Petersen, Farum (DK)

(73) Assignee: BerGenBio AS, Bergen (NO)

( * ) Notice: Subject to any disclaimer, the term of this patent is extended or adjusted under 35 U.S.C. 154(b) by 0 days. days.

(21) Appl. No.: 15/526,220

(22) PCT Filed: Nov. 13, 2015

(86) PCT No.: PCT/GB2015/053442
§ 371 (c)(1),
(2) Date: May 11, 2017

(87) PCT Pub. No.: WO2016/075477
PCT Pub. Date: May 19, 2016

(65) Prior Publication Data
US 2017/0334884 A1     Nov. 23, 2017

(30) Foreign Application Priority Data

Nov. 14, 2014 (GB) .................................. 1420285.7

(51) Int. Cl.
*C07D 403/14* (2006.01)

(52) U.S. Cl.
CPC .................................. *C07D 403/14* (2013.01)

(58) Field of Classification Search
CPC .................................................... C07D 403/14
See application file for complete search history.

(56) References Cited

FOREIGN PATENT DOCUMENTS

| WO | 2008/083367 A2 | 7/2008 |
| WO | 2010/005876 A2 | 1/2010 |
| WO | 2010/083465 A1 | 7/2010 |
| WO | 2016/075477 A1 | 5/2016 |

OTHER PUBLICATIONS

Holland et al., "R428, a Selective Small Molecule Inhibitor of Axl Kinase, Blocks Tumor Spread and Prolongs Survival in Models of Metastatic Breast Cancer", Cancer Research, 2010, pp. 1544-1554, vol. 70, No. 4.

International Search Report and Written Opinion from International Application No. PCT/GB2015/053442, dated Jan. 20, 2016; 9 pgs.

*Primary Examiner* — Paul V Ward

(57) ABSTRACT

A process for purifying 1-(6,7-dihydro-5H-benzo[6,7]cyclohepta[1,2-c]pyridazine-3-yl)-$N^3$-(7-(pyrrolidin-1-yl)-6,7,8,9-tetrahydro-5H-benzo[7]annulene-2-yl)-1H-1,2,4-triazole-3,5-diamine free base is described, the process comprising a) dissolving a quantity of crude 1-(6,7-dihydro-5H-benzo[6,7]cyclohepta[1,2-c]pyridazine-3-yl)-$N^3$-(7-(pyrrolidin-1-yl)-6,7,8,9-tetrahydro-5H-benzo[7]annulene-2-yl)-1H-1,2,4-triazole-3,5-diamine in a mixed solvent of $C_{1-5}$ alcohol and water, together with an acid, and b) increasing the pH of the solution resulting from (a) until 1-(6,7-dihydro-5H-benzo[6,7]cyclohepta[1,2-c]pyridazine-3-yl)-$N^3$-(7-(pyrrolidin-1-yl)-6,7,8,9-tetrahydro-5H-benzo[7]annulene-2-yl)-1H-1,2,4-triazole-3,5-diamine free base is precipitated from the alcohol-water mixed solvent.

25 Claims, 2 Drawing Sheets

Figure 1:
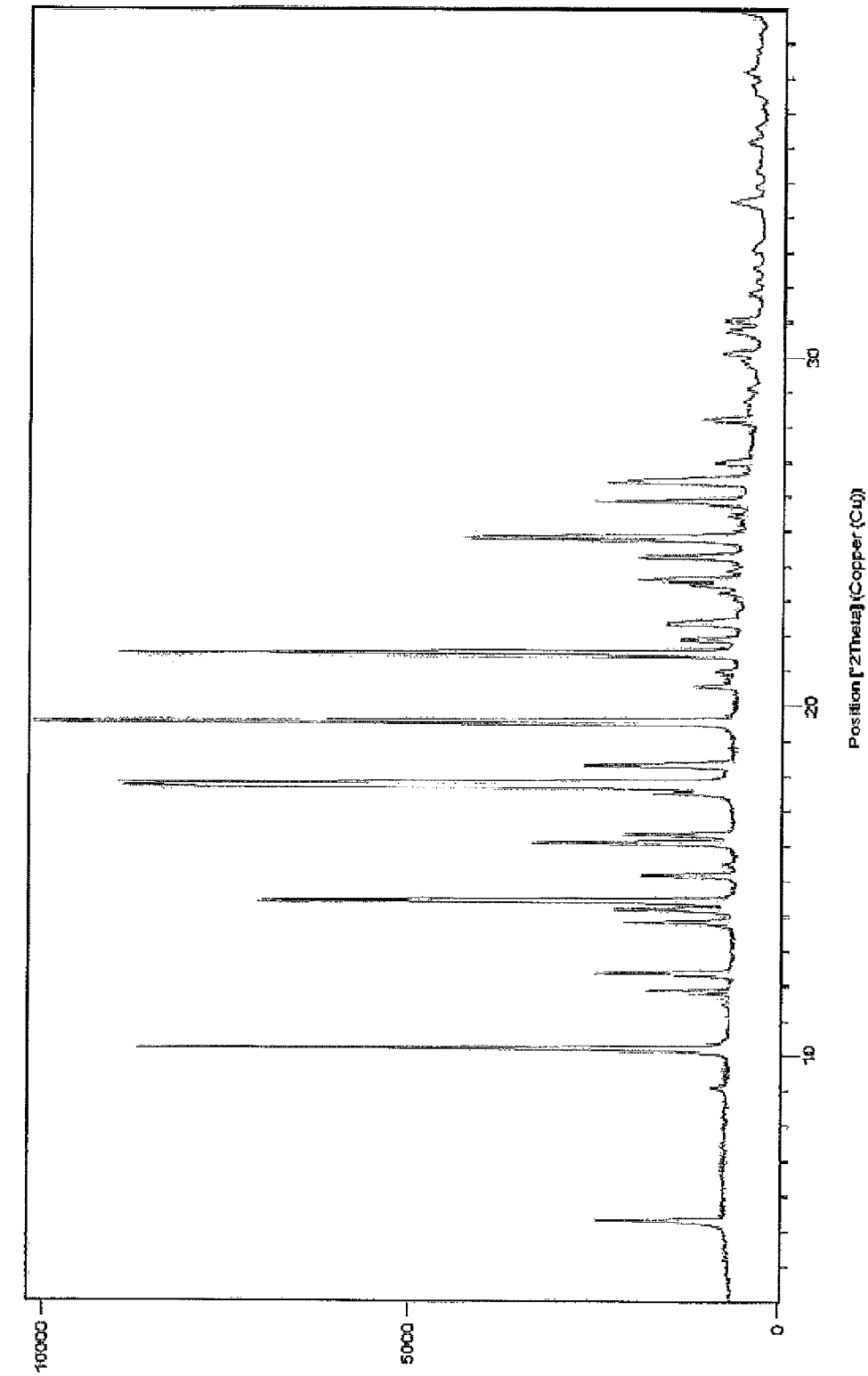

PROCESS FOR THE PURIFICATION OF THE AXL TYROSINE RECEPTOR KINASE INHIBITOR "R428"

This invention relates to a process, in particular a process for obtaining the free base of a defined active pharmaceutical ingredient in a form having high purity and low solvent residues.

Axl (also known as UFO, ARK, and Tyro1; nucleotide accession numbers NM_021913 and NM_001699; protein accession numbers NP_068713 and NP_001690) is a receptor protein tyrosine kinase (RTK) that comprises a N-terminal extracellular ligand-binding domain and C-terminal cytoplasmic region containing the catalytic domain. Axl and its two close relatives, MerTK/Nyk and Sky (Tyro3/Rse/Dtk), collectively known as the TAM family of RTK's, all bind and are stimulated to varying degrees by the same ligand, Gas6 (growth arrest specific-6), a ~76 kDa secreted protein with significant homology to the coagulation cascade regulator, Protein S. In addition to binding to ligands, the Axl extracellular domain has been shown to undergo homophilic interactions that mediate cell aggregation, suggesting that one important function of Axl may be to mediate cell-cell adhesion.

In WO2008/083367, a group of compounds are disclosed as inhibitors of Axl. Such inhibition is shown to lead to antineoplastic effects. One particular compound, 1-(6,7-dihydro-5H-benzo[6,7]cyclohepta[1,2-c]pyridazine-3-yl)-$N^3$-(7-(pyrrolidin-1-yl)-6,7,8,9-tetrahydro-5H-benzo[7]annulene-2-yl)-1H-1,2,4-triazole-3,5-diamine (hereinafter sometimes referred to as compound A), has been shown to be particularly promising in this regard. The small-scale synthesis of compound A described in WO2008/083367 is carried out in isopropyl alcohol, with subsequent evaporation of the solvent and purification by HPLC. However, such a procedure is expensive and not amenable to scaling-up. Other approaches to isolating the free base of compound A have been attempted, but these typically involve too many steps and have a risk of providing a product with higher solvent residues than may be desired. For example, following synthesis of compound A in a final solvent comprising toluene, one approach to isolation involved exchanging toluene for methanol by distillation, followed by addition of dichloromethane, drying using MgSO$_4$, removal of DCM by distillation, addition of methanol, addition of fumaric acid to the hot solvent and precipitation and isolation of the fumarate salt. This salt was then treated with a mixture of aqueous potassium carbonate, ethanol and DCM, the organic phase was dried, filtered and evaporated to give an impure compound A free base. This was redissolved in ethanol/DCM, and fed into boiling ethanol, with removal of DCM by distillation, resulting in precipitation of compound A free base. Even after this complex process, however, levels of residual ethanol and DCM in the product were higher than desired, unpredictable and affected significantly by the scale of the process.

It is therefore an object of the present invention to provide a process for the purification of the free base of compound A which is susceptible of scale-up and which provides a product with acceptably low solvent residues.

In accordance with a first aspect of the invention, there is provided a process for purifying 1-(6,7-dihydro-5H-benzo[6,7]cyclohepta[1,2-c]pyridazine-3-yl)-$N^3$-(7-(pyrrolidin-1-yl)-6,7,8,9-tetrahydro-5H-benzo[7]annulene-2-yl)-1H-1,2,4-triazole-3,5-diamine free base, the process comprising a) dissolving a quantity of crude 1-(6,7-dihydro-5H-benzo[6,7]cyclohepta[1,2-c]pyridazine-3-yl)-$N^3$-(7-(pyrrolidin-1-yl)-6,7,8,9-tetrahydro-5H-benzo[7]annulene-2-yl)-1H-1,2,4-triazole-3,5-diamine in a mixed solvent of $C_{1-5}$ alcohol and water, together with an acid, and b) increasing the pH of the solution resulting from (a) until 1-(6,7-dihydro-5H-benzo[6,7]cyclohepta[1,2-c]pyridazine-3-yl)-$N^3$-(7-(pyrrolidin-1-yl)-6,7,8,9-tetrahydro-5H-benzo[7]annulene-2-yl)-1H-1,2,4-triazole-3,5-diamine free base is precipitated from the alcohol-water mixed solvent.

The process of the invention provides a facile means for recovering a relatively pure form of compound A free base from a crude sample. The term 'crude' as used herein simply refers to a form of the compound A which is less pure (in terms of free base) than is desired for the intended use. The crude sample may, for example, come from a reaction mixture in which compound A has been synthesised. The compound A free base can be obtained without the necessity of using harmful and/or water-immiscible organic solvents. In addition, there is no need to proceed via the additional steps of isolating the compound A-acid salt, followed by breaking of the salt back to the free base. The pH increase during step (b) leads to generation of the less soluble free base of compound A, which precipitates, leaving the more soluble compound A-acid salt in solution. The process leads to a suitable purity product in high yield, and with low solvent residues, for example significantly below 10,000 ppm ethanol, when this is used as the $C_{1-5}$ alcohol in the mixed solvent. In addition, the process of the invention leads to a product having a high polymorphic purity with respect to the most pharmaceutically useful polymorphic form of compound A free base.

The term 'crude compound A' is intended to include salt forms of compound A. Thus, the process of the invention may be used to purify compound A free base from a sample of a salt of compound A. In such embodiments, it will be appreciated that the acid to be dissolved in step (a) may simply be the conjugate acid of the compound A salt used as the crude compound A, such that no additional acid may be required to be added.

In the process of the invention, the alcohol in the alcohol-water mixed solvent (i.e. the mixed solvent of $C_{1-5}$ alcohol and water) is preferably methanol or ethanol, although other straight or branched chain $C_{1-5}$ alcohols can also be used. The preferred alcohol is ethanol, and the mixed solvent based thereon provides a good extraction of compound A from the crude input material.

In preferred embodiments, the alcohol-water mixed solvent, prior to carrying out step (b), is adjusted (if necessary) such that it contains 60-80%, preferably 70-80% alcohol by volume. Solvent compositions at this level have been found to work well in the precipitation of step (b). Alcohol contents outside the 70-80% range may still allow for the process of the invention to be successfully employed (for example, 60% ethanol by volume has been found to yield useful results); however, it has been found that alcohol contents in the 70-80% range unexpectedly provide even better results. If the alcohol-water mixed solvent composition used in step (a) already has the required alcohol content by volume, this adjustment step may not be necessary. However, if it is necessary or desirable to use a lower alcohol content mixed solvent for step (a), further alcohol can be added before step (b) is carried out to bring the alcohol content to the required level. Where the crude compound A is presented in the form of a reaction mixture in which compound A has been synthesised, this will often be in the form of a solution in a non-polar solvent (for example, toluene or dichloromethane). In such cases, a lower alcohol content mixed solvent may be used in step (a) to ensure a clean phase separation between the non-polar solvent and the alcohol-water mixed solvent, and thus an efficient removal of the non-polar solvent and impurities, and minimal loss of the compound A.

The alcohol-water mixed solvent, prior to carrying out step (b), may for example be adjusted (if necessary) such that it contains 73-77% alcohol by volume, preferably approximately 75% alcohol by volume. Particularly in the case of ethanol, such solvent compositions have been found to provide for surprisingly efficient precipitation in step (b).

In step (b), the pH of the resulting solution from (a) may be increased, for example, to 7.5 to 9.5. In particular, the pH may be increased to 7.8 to 8.8, preferably approximately 8.5. It has been found that an increase in pH to within the stated ranges leads to efficient precipitation of compound A free base, with minimal co-precipitation of impurities.

The pH of the resulting solution from (a) may conveniently be increased in step (b) using a solution of a base. The base is preferably an inorganic base, although suitable organic bases may also be employed. Preferred bases include NaOH and KOH, particularly KOH. The use of a base comprising KOH leads to a reduction in the appearance of insoluble impurities in the compound A free base.

It may be necessary, in some embodiments, to increase the pH more than once during step (b), in particular once precipitation has commenced. This is because precipitation of compound A free base can lead to a drop in the pH. This may be less of a problem if the crude compound A is presented in step (a) in the form of a reaction mixture in which compound A has been synthesised, since the other components of the reaction mixture may buffer the solution to an extent.

In preferred embodiments, the solution of a base used to increase the pH in step (b) employs an alcohol-water mixed solvent having substantially the same solvent composition as the alcohol-water mixed solvent in which the crude compound A is presented for this step. This ensures that the composition of the alcohol-water mixed solvent does not change as a result of the base addition. Since the precipitation can be sensitive to the alcohol content, this precaution can be usefully deployed.

In step (a), the dissolution of the crude compound A, and the acid, in the mixed solvent of $C_{1-5}$ alcohol and water may be performed at elevated temperature (e.g. above 60 degrees C., preferably above 65 degrees C., more preferably above 70 degrees C.). Enhanced and/or more rapid dissolution may be obtained in this manner. Whether or not dissolution is performed at elevated temperature, it is preferred that the temperature of the resulting solution from (a) is maintained at 70 degrees C. or more while the pH is increased (i.e. during step (b)). This is to ensure that the salt formed between compound A and the acid remains dissolved, thereby preventing it from contaminating the free base precipitate to be formed in step (b). In preferred embodiments, the temperature of the resulting solution from (a) is maintained at 73 degrees C. or more in step (b) until precipitation of compound A free base commences. In certain instances, better results may be obtained if the solution is maintained at around 75 degrees C. during precipitation, at least during the initial phases thereof. Once precipitation is underway, cooling of the solution may be undertaken, but precipitation progress should ideally be monitored. Useful results have, for example, been obtained by allowing the mixture to cool naturally from 75 degrees C. to ambient temperature, e.g. such that the mixture cools by around 8 to 9 degrees C. per hour (on average) over the first 4 to 5 hours.

The process of the invention may also comprise the further steps of:
c) redissolving the precipitated 1-(6,7-dihydro-5H-benzo[6,7]cyclohepta[1,2-c]pyridazine-3-yl)-$N^3$-(7-(pyrrolidin-1-yl)-6,7,8,9-tetrahydro-5H-benzo[7]annulene-2-yl)-1H-1,2,4-triazole-3,5-diamine free base obtained in step (b) in a mixed solvent of $C_{1-5}$ alcohol and water, together with an acid, and
d) increasing the pH of the resulting solution from (c) until 1-(6,7-dihydro-5H-benzo[6,7]cyclohepta[1,2-c]pyridazine-3-yl)-$N^3$-(7-(pyrrolidin-1-yl)-6,7,8,9-tetrahydro-5H-benzo[7]annulene-2-yl)-1H-1,2,4-triazole-3,5-diamine free base is precipitated from the alcohol-water mixed solvent.

Steps (c) and (d) provide a re-precipitation of the compound A free base obtained in step (b). This leads to a further increase in purity of the compound A free base. Following the process of step (a) and step (b) alone, purities of around 98% w/w were obtained. Following re-precipitation as per steps (c) and (d), the purity was increased to greater than 99% w/w. Moreover, steps (c) and (d) lead to a product having an even higher polymorphic purity with respect to the desired polymorphic form of compound A free base.

In carrying out the re-precipitation procedure, it may be useful, during precipitation of compound A free base in step (d), to increase the pH further, as necessary, to maintain a pH at or above the level at which precipitation of compound A free base commences in step (d). As described above in the context of step (b), this may be necessary since the precipitation of compound A free base can lead to a drop in pH. This can be monitored for and attenuated by the addition of further base, for example. The elevated temperature conditions mentioned above in the context of step (a) may also be employed for step (c). Equally, the temperature and cooling conditions mentioned above with respect to step (b) may also be advantageously employed in carrying out step (d).

The acid used in step (a) and/or step (c) may be selected from fumaric, citric and hydrochloric acid. Other acids may be used, as would be appreciated by the skilled person.

In certain embodiments, 1-(6,7-dihydro-5H-benzo[6,7]cyclohepta[1,2-c]pyridazine-3-yl)-$N^3$-(7-(S)-(pyrrolidin-1-yl)-6,7,8,9-tetrahydro-5H-benzo[7]annulene-2-yl)-1H-1,2,4-triazole-3,5-diamine free base (i.e. the S-enantiomer of compound A free base) is purified from a crude quantity of 1-(6,7-dihydro-5H-benzo[6,7]cyclohepta[1,2-c]pyridazine-3-yl)-$N^3$-(7-(S)-(pyrrolidin-1-yl)-6,7,8,9-tetrahydro-5H-benzo[7]annulene-2-yl)-1H-1,2,4-triazole-3,5-diamine (i.e. crude S-enantiomer of compound A).

Usefully, the crude compound A may be the product of a reaction between phenyl N'-cyano-N-(7-(pyrrolidin-1-yl)-6,7,8,9-tetrahydro-5H-benzo[7]annulen-2-yl)carbamimidate and 3-hydrazino-6,7-dihydro-5H-benzo[6,7]cyclohepta[1,2-c]pyridazine Such a reaction is described in the prior art (for example WO2008/083367). This reaction may be carried out in any suitable solvent, and the crude compound A may be presented for step (a) in either solid or solution form (referred to herein as a 'starting solution'). As described above, non-polar solvents may conveniently be used, since step (a) may then comprise a solution-phase extraction of the compound A, with impurities being retained in the non-polar solvent.

Thus, in embodiments, a starting solution of the crude compound A is brought into contact with the alcohol-water mixed solvent in step (a). The starting solution of the crude compound A may comprise a product solution resulting from the reaction between phenyl N'-cyano-N-(7-(pyrrolidin-1-yl)-6,7,8,9-tetrahydro-5H-benzo[7]annulen-2-yl)carbamimidate and 3-hydrazino-6,7-dihydro-5H-benzo[6,7]cyclohepta[1,2-c]pyridazine. As explained above, the starting solution may conveniently employ a solvent other than the alcohol-water mixed solvent used in step (a). In certain embodiments, the solvent of the starting solution may be substantially immiscible with the alcohol-water mixed solvent used in step (a). Usually, the solvent of the starting solution is conveniently removed prior to step (b).

In accordance with a second aspect, the present invention provides 1-(6,7-dihydro-5H-benzo[6,7]cyclohepta[1,2-c]pyridazine-3-yl)-N³-(7-(pyrrolidin-1-yl)-6,7,8,9-tetrahydro-5H-benzo[7]annulen-2-yl)-1H-1,2,4-triazole-3,5-diamine free base, or 1-(6,7-dihydro-5H-benzo[6,7]cyclohepta[1,2-c]pyridazine-3-yl)-N³-(7-(S)-(pyrrolidin-1-yl)-6,7,8,9-tetrahydro-5H-benzo[7]annulene-2-yl)-1H-1,2,4-triazole-3,5-diamine free base, obtained or obtainable by the process of the first aspect of the invention.

Figure 2:
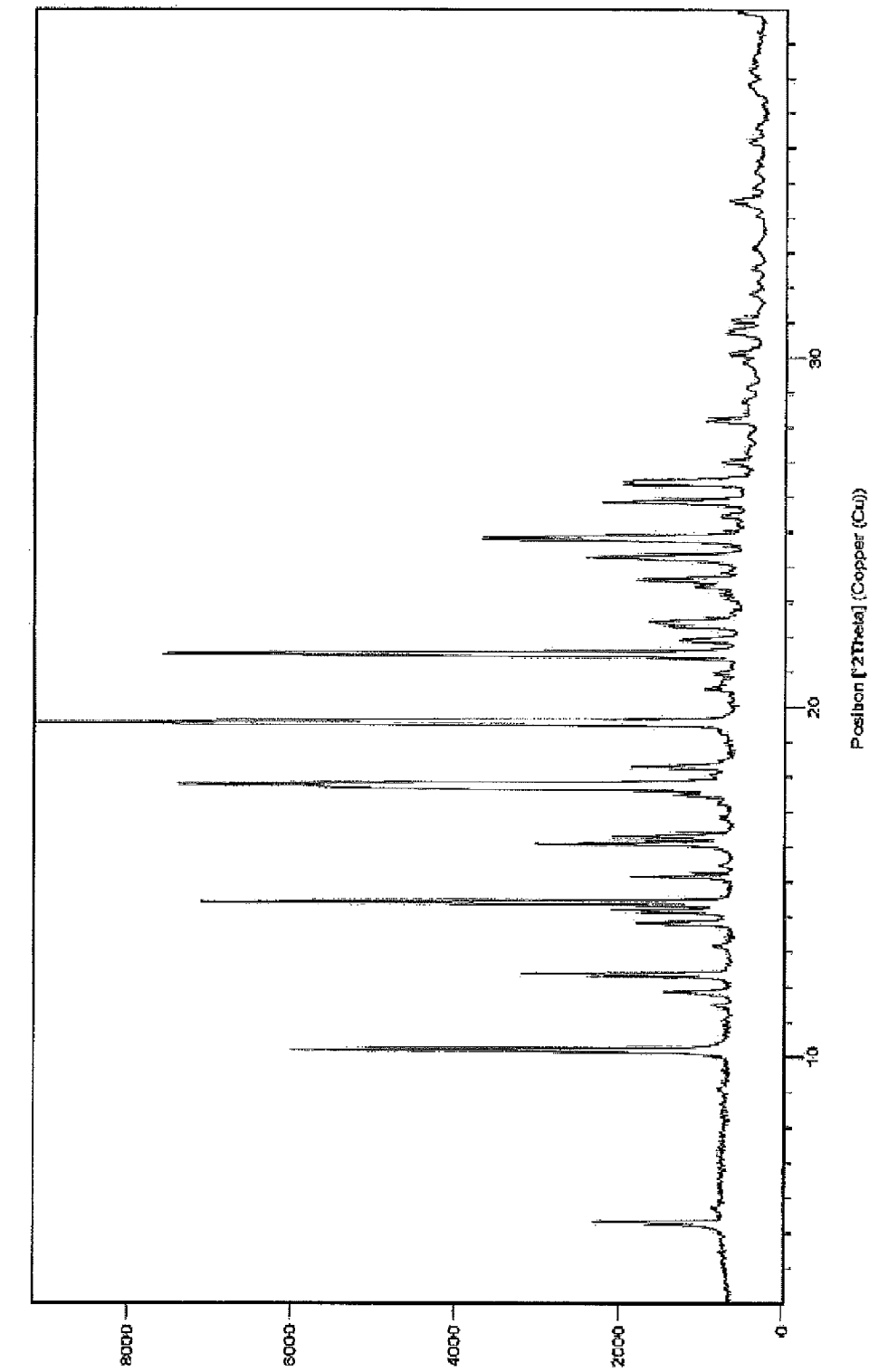

The invention will now be described in more detail by way of example only and with reference to the appended Figures, of which:

FIG. 1 shows the XRPD results from a sample of compound A free base, obtained by the process of the invention using steps (a), (b), (c) and (d); and FIG. 2 shows the XRPD of a reference sample of compound A free base, having the desired polymorphic form.

Synthesis of Compound A

A route for the last step in the synthesis of compound A is illustrated in Scheme 1. B* was dissolved in toluene and reacted with DPCC at 30° C. When the conversion was complete, compound F was charged, and the temperature was increased to 65° C.

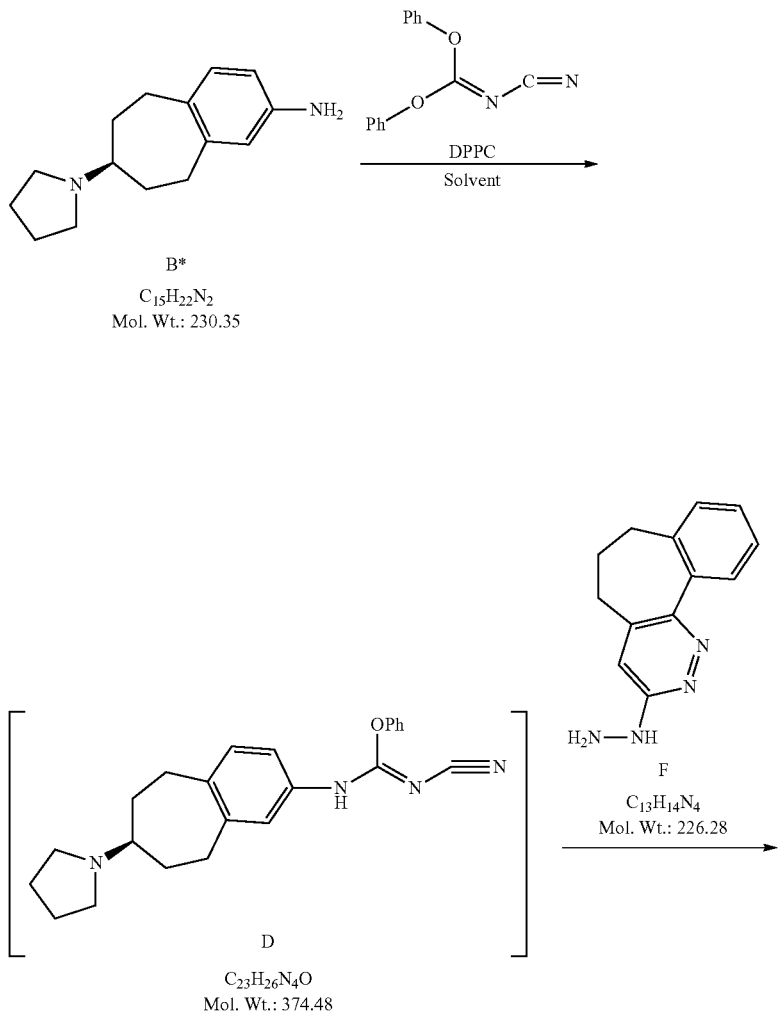

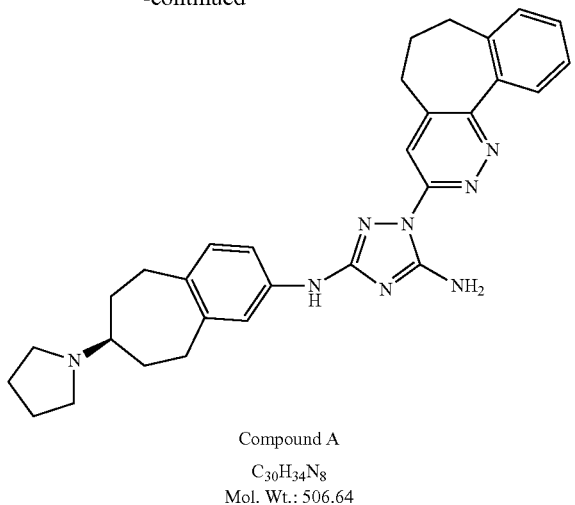

Compound A
C$_{30}$H$_{34}$N$_8$
Mol. Wt.: 506.64

Three experiments (0.1 g B*) were set up in three different solvents: toluene, isopropanol and acetonitrile. The best outcome, at least in terms of solubility of D, was in toluene. All reactions were left overnight, and in most cases, the reaction mixture was a brown solution with a little precipitated solid around the edges. Conversion of B* to D was generally over 99%, and yield of compound A was generally around 70% or more (by HPLC).

Work-Up

Compound A fumarate salt material was tested for solubility in 50% methanol/water, 75% methanol/water, 50% ethanol/water and 75% ethanol/water. The fumarate salt dissolved in all cases (heating). Attempts to re-precipitate by adding NaOH were successful from 75% ethanol/water.

The preferred solvent mixture was ethanol/water, and an extraction of the reaction mixture was performed, where compound A would end up in the ethanol/water phase. Adding ethanol, water and fumaric acid (1 eq. compared with the theoretical yield) to the reaction mixture at 50° C. to give a 1:1:1 mixture of ethanol/water/toluene resulted in a phase separation and minimal loss of product in the toluene phase.

Precipitation of Compound A Free Base

Prior to precipitating, the reaction mixture was filtered (hot) in order to remove particles. A substantial amount of ethanol was used to "wash in" the product in order to get an approximately 75% ethanol/water mixture. Initially, the precipitation was done at 75° C. by addition of 1M NaOH (aq), with pH adjusted to 9.1. The suspension was allowed to cool overnight. Compound A was isolated in 62% yield with a purity of 97.3%. When pH was adjusted to 10.5 in a similar experiment, more or less the same yield was obtained (63%), but the purity had dropped to 93.9%. Furthermore, some carry-over of fumaric acid was detected.

Adding KOH instead of NaOH resulted in solutions at higher pH. Therefore, a precipitation was done with 1M KOH (aq.) by adjusting pH to 9 at 75° C. After cooling overnight, compound A free base was isolated in 56% yield, with a purity of 95.3%.

As pH in the latter experiments had been adjusted with aqueous base, it was calculated that the actual ethanol/water ratio was 63-67%. A repeat was therefore carried out, starting from 10 g B*, and after the work-up, the solution was split into two portions. In both cases pH was adjusted with 1M KOH in 75% ethanol/water, thereby keeping the ethanol/water ratio constant. The first experiment was adjusted to pH 8.5, and the second experiment was adjusted to pH 9.0. After precipitation overnight, pH was measured to 9.3 and 10.1, respectively. The reason for the increase in pH is the decrease in temperature. The first experiment resulted in a 50% yield with a purity of 98.7%. The second resulted in a 43% yield with a purity of 98.5%. It was concluded that keeping the ethanol/water ratio at 75% ethanol was definitely beneficial, and precipitation at pH 8.5 gave the best result.

Scale up of the latter experiment was carried out to 20 g B*. This proceeded satisfactorily with a yield of 21.2 g (54%) and a purity of 97.6%. In addition, scale-up to 120 g B* was carried out. This also proceeded satisfactorily, and 174.9 g wet solid was isolated. Based on drying of a small sample, the yield was determined to be 51% with a purity of 98.7%.

Re-Precipitation of Compound A, Free Base

The re-precipitation was tested, using the material from the above experiment with a purity of 97.6%. The material was divided into 2×10 g and precipitated either at pH 9.0 or at pH 8.5. The solvent mixture was set at 75% ethanol/water, amount of fumaric acid at 0.75 eq., temperature at 75° C., base at 1M KOH in 75% ethanol/water and time at overnight.

The pH 9.0 experiment produced 7.5 g of free base (75% recovery) with a purity of 99.3%, assay of 98.8%, residual ethanol of 14,600 ppm and water content of 0.20%. XRPD was performed on a sample of the compound A free base so obtained, and the results are shown in FIG. 1. Excellent comparison with the reference sample XRPD (FIG. 2) can be observed. In the experiment in which pH was adjusted to 8.5 and then left to cool, it turned out that this pH was potentially lower than optimal, as pH dropped when the compound precipitated, such that more compound A than desired was found in the filtrate after cooling.

Therefore, in a subsequent run, pH was adjusted with 1M KOH in 75% ethanol/water, and at pH 8.0 spontaneous precipitation was observed. pH was allowed to stabilize without addition of base (stable at pH 7.5), and then adjusted to 8.5 by addition of base. Again pH was stabilized at 8.5 by addition of base. When stable pH had been observed for 20 min, the suspension was allowed to cool overnight. After 85 min the temperature was 46° C., and after overnight cooling pH was measured to 9.4 (22.0° C.). 2.63 g was isolated (88% recovery) with a purity of 99.4%, and residual ethanol of 8,800 ppm.

This re-precipitation was very successful and well controlled.

Discussion and Conclusions

It was found that adding ethanol, water and fumaric acid (1 eq. compared with the theoretical yield) to the reaction mixture from the synthesis of compound A to give a 1:1:1 ratio between the solvents (toluene:ethanol:water), resulted in a separating solution (at 50° C.), where the toluene was removed with a minimal loss of product and removal of some impurities. An extra wash with toluene removed further impurities with a minimal loss of product, and excess toluene could be removed by azeotropic distillation.

Ethanol was added to the ethanol/water phase to get an approximate 75% ethanol/water mixture. The precipitation was done at 75° C. by pH adjustment to 8.5 with 1M KOH in 75% ethanol/water. Using the final precipitation method, Purities of 97.6%-98.9% were obtained, and yields of 50%-54%.

The following factors were found to be important to the precipitation:
  The base: When using NaOH to adjust pH some insoluble material was formed. When changing to KOH this was not a problem.
  pH: The higher pH the more impure compound. pH 8.5 has been shown to give the best result. pH does not drop significantly when the compound precipitates, probably due to buffering from the reaction mixture.
  Alcohol/water ratio: A great improvement in purity was observed when 1M KOH in 75% ethanol/water was used to adjust pH instead of aqueous KOH, thereby preserving the ethanol/water ratio at 75%.
  Temperature: There is an influence of temperature. For example, the fumarate salt of compound A dissolves at >70° C., and it would appear less advantageous to precipitate at <73° C. It may be beneficial to allow the precipitate to mature at 75° C. and cool slowly. Even better results may, of course, be obatined when cooling in a more controlled manner, as would be appreciated by the skilled person.

Screening experiments on 1 g scale were done in order to investigate the re-precipitation. Larger scale experiments were also performed, providing recoveries of 85-88% and purities of 99.4%-99.7%, and residual ethanol levels of 7,400-8,800 ppm.

The following parameters were found to be important for the re-precipitation:
  The base: KOH was found to be effective in all re-precipitation experiments
  pH: When precipitation starts the pH may drop. It is therefore beneficial to control and adjust pH. In the experiments described above, once precipitation started, it was useful to wait until pH had stabilized. In two of three large experiments, spontaneous precipitation was observed at pH 8.0, and it might be beneficial to seed already at pH 7.8. Final adjustment to pH 8.5 and stabilization at this pH was sufficient to give satisfactory purities and recoveries. pH rises upon cooling, and even though the final pH has varied from 9.2 to 9.8, the quality of the isolated lots was similar. The pH measurement was conducted using a WTW, pH3110 pH meter containing a thermosensor. It was calibrated at 20 degrees C.
  Time: It was beneficial to allow crystals to grow at high temperature, followed by slow cooling in a controlled manner.
  Alcohol/water ratio: 75% ethanol/water was used in the above experiments, but good residual ethanol levels have also been seen when more water was added. More water might affect the purity in a negative sense, but if the starting material already has a high purity, this is not as important.
  Temperature: Precipitating the compound at >73° C. provides good results, especially if the precipitate is allowed to mature at this temperature.

Overall, the process of the invention is simple, avoiding the use of unfavourable solvents, and avoiding several solvent changes. No isolation of the fumarate (or other acid) salt of compound A is required; instead compound A free base can isolated direct, and re-precipitated without drying. The overall yield of the final reaction and the largest re-precipitation experiment was a respectable 43%. The residual ethanol was significantly <10,000 ppm.

Analytical Methods

HPLC analyses were performed as described below: A1—HPLC method for determining the conversion of B* to D; A2—HPLC method for D and F to compound A, and compound A purity.

A1: HPLC, IPC Method for the Conversion of B* to D
HPLC column: Phenomenex Gemini NX, C18, 3 μm, 150× 4.6 mm
Flow: 1.0 mL/min
Injection volume: 3 μL
Detection wavelength: 240 nm
Column temperature: 30° C.
Autosampler temperature: 20° C.
Mobile phase A: 0.1% DEA in MQ-water
Mobile phase B: Acetonitrile
Sample solvent: 0.1% TFA in methanol/MQ-water, 1:1
Sample preparation: 10 μL of reaction mixture is evaporated and re-dissolved in 1 ml of SS
Gradient Profile

| Total time (min) | Mobile phase A (%) | Mobile phase B (%) |
|---|---|---|
| 0 | 90 | 10 |
| 10 | 65 | 35 |
| 15 | 30 | 70 |
| 20 | 5 | 95 |
| 20.1 | 90 | 10 |
| 28 | 90 | 10 |

Approximate Retention Times

| Phenol: | 2 min |
|---|---|
| D: | 11.0 min |
| B*: | 15.9 min |

HPLC Method A2:
HPLC column: Zorbax Eclipse XDB-C18, 4.6×100 mm
Flow: 1.0 mL/min
Injection volume: 10 μL
Detection wavelength: 255 nm
Column temperature: 55° C.
Autosampler temperature: 20° C.
Mobile phase A: 0.1% TFA in MQ-water
Mobile phase B: 0.1% TFA in methanol/acetonitrile, 1:1

Sample solvent: 0.1% TFA in methanol/MQ-water, 1:1
Nominal concentration: 180 µg/mL
Sample preparation (IPC): 8 µL of reaction mixture is evaporate and re-dissolved in 1 mL of SS.
Gradient Profile

| Total time (min) | Mobile phase A (%) | Mobile phase B (%) |
| --- | --- | --- |
| 0 | 70 | 30 |
| 1 | 70 | 30 |
| 6 | 50 | 50 |
| 17 | 5 | 95 |
| 17.1 | 70 | 30 |
| 22 | 70 | 30 |

Approximate Retention Times

| | |
| --- | --- |
| Phenol: | 4.4 min |
| F: | 5.1 min |
| D: | 6.9 min |

Retention time of compound A was 10.4 min.
Residual ethanol was determined by gas chromatography analysis as per A3 below.
A3: Residual Ethanol Analysis by GC
Column: Agilent DB-1, Part #123-1064 (60 m×320 µm ID×3.0 µm)
Carrier gas: Helium
Mode: Constant pressure 1.2 bar
Oven: Init. Temp.: 40° C.
  Initial isothermal time: 9.0 min.
  Rate 1: 26.3° C./min.
  Temp. 1: 145° C.
  Isothermal time: 7.0 min.
  Rate 2: 67.5° C./min.
  Final temperature: 280° C./min.
  Final isothermal time: 11.0 min.
Inlet: Mode: Split
  Liner: Split/splitless
  Split ratio: 5.0
  Temp.: 250° C.
Gas saver: Off
Detector (FID) Temp.: 280° C.
  $H_2$ flow: 40.0 mL/min.
  Air flow: 450.0 mL/min.
  Mode: Constant make up
  Make up: 30.0 mL/min.
Injector: Volume: 1.0 µl
  Sample diluent: DMSO
  Sample preparation: Dissolve ~100 mg of accurately weighed compound A in ~5 mL of DMSO by sonication. Allow to cool and fill to volume (5.0 mL) with DMSO.
  Needle Wash Solvent: DMSO
Water analysis was carried out using Karl-Fischer titration using methanol/dichloromethane, 3:1 as the solvent. Extraction time was 180 s.
XRPD analysis: Performed using a Panalytical Xpert Pro diffractometer using Cu Kα X-ray radiation and a Pixcel detector system. The samples were held between low density polyethylene films and analysed at ambient temperature in transmission mode. Instrument parameters: range 3-40°2θ, step size 0.013°, counting time 99 sec, ~22 min run time). XRPD patterns were sorted, manipulated and indexed using HighScore Plus 2.2c software.

The invention claimed is:
1. A process for purifying 1-(6,7-dihydro-5H-benzo[6,7]cyclohepta[1,2-c]pyridazine-3-yl)-$N^3$-(7-(pyrrolidin-1-yl)-6,7,8,9-tetrahydro-5H-benzo[7]annulene-2-yl)-1H-1,2,4-triazole-3,5-diamine free base, the process comprising
  a) dissolving a quantity of crude 1-(6,7-dihydro-5H-benzo[6,7]cyclohepta[1,2-c]pyridazine-3-yl)-$N^3$-(7-(pyrrolidin-1-yl)-6,7,8,9-tetrahydro-5H-benzo[7]annulene-2-yl)-1H-1,2,4-triazole-3,5-diamine in a mixed solvent of $C_{1-5}$ alcohol and water, together with an acid,
  b1) increasing the pH of the solution resulting from (a) until 1-(6,7-dihydro-5H-benzo[6,7]cyclohepta[1,2-c]pyridazine-3-yl)-$N^3$-(7-(pyrrolidin-1-yl)-6,7,8,9-tetrahydro-5H-benzo[7]annulene-2-yl)-1H-1,2,4-triazole-3,5-diamine free base is precipitated from the alcohol-water mixed solvent, and
  b2) isolating the precipitated 1-(6,7-dihydro-5H-benzo[6,7]cyclohepta[1,2-c]pyridazine-3-yl)-$N^3$-(7-(pyrrolidin-1-yl)-6,7,8,9-tetrahydro-5H-benzo[7]annulene-2-yl)-1H-1,2,4-triazole-3,5-diamine free base from the alcohol-water mixed solvent.
2. The process according to claim 1, wherein the alcohol in the alcohol-water mixed solvent is ethanol.
3. The process according to claim 1, wherein the alcohol-water mixed solvent, prior to carrying out step (b1), is adjusted if necessary such that it contains 60-80% alcohol by volume.
4. The process according to claim 3, wherein the alcohol-water mixed solvent, prior to carrying out step (b1), is adjusted if necessary such that it contains 73-77% alcohol by volume.
5. The process according to claim 1, wherein, in step (b1), the pH of the resulting solution from (a) is increased to 7.5 to 9.5.
6. The process according to claim 5, wherein, in step (b1), the pH is increased to 7.8 to 8.8.
7. The process according to claim 1, wherein, in step (b1), the pH of the resulting solution from (a) is increased using a solution of a base.
8. The process according to claim 7, wherein the solution of a base used to increase the pH in step (b1) employs an alcohol-water mixed solvent having substantially the same solvent composition as the alcohol-water mixed solvent in which the crude 1-(6,7-dihydro-5H-benzo[6,7]cyclohepta[1,2-c]pyridazine-3-yl)-$N^3$-(7-(pyrrolidin-1-yl)-6,7,8,9-tetrahydro-5H-benzo[7]annulene-2-yl)-1H-1,2,4-triazole-3,5-diamine is presented for this step.
9. The process according to claim 1, wherein, in step (b1), the pH of the resulting solution from (a) is increased using a base comprising potassium hydroxide.
10. The process according to claim 1, wherein, in step (a), the dissolution of the crude 1-(6,7-dihydro-5H-benzo[6,7]cyclohepta[1,2-c]pyridazine-3-yl)-$N^3$-(7-(pyrrolidin-1-yl)-6,7,8,9-tetrahydro-5H-benzo[7]annulene-2-yl)-1H-1,2,4-triazole-3,5-diamine, and the acid, in the mixed solvent of $C_{1-5}$ alcohol and water is performed at elevated temperature.
11. The process according to claim 10, wherein, in step (b1), the temperature of the resulting solution from (a) is maintained at 70 degrees C. or more while the pH is increased.
12. The process according to claim 1, wherein, in step (b1), the temperature of the resulting solution from (a) is maintained at 73 degrees C. or more until precipitation of 1-(6,7-dihydro-5H-benzo[6,7]cyclohepta[1,2-c]pyridazine-3-yl)-$N^3$-(7-(pyrrolidin-1-yl)-6,7,8,9-tetrahydro-5H-benzo[7]annulene-2-yl)-1H-1,2,4-triazole-3,5-diamine free base commences.

13. The process according to claim 1, comprising the further steps of:
- c) redissolving the precipitated 1-(6,7-dihydro-5H-benzo[6,7]cyclohepta[1,2-c]pyridazine-3-yl)-$N^3$-(7-(pyrrolidin-1-yl)-6,7,8,9-tetrahydro-5H-benzo[7]annulene-2-yl)-1H-1,2,4-triazole-3,5-diamine free base obtained in step (b2) in a mixed solvent of $C_{1-5}$ alcohol and water, together with an acid,
- d1) increasing the pH of the resulting solution from (c) until 1-(6,7-dihydro-5H-benzo[6,7]cyclohepta[1,2-c]pyridazine-3-yl)-$N^3$-(7-(pyrrolidin-1-yl)-6,7,8,9-tetrahydro-5H-benzo[7]annulene-2-yl)-1H-1,2,4-triazole-3,5-diamine free base is precipitated from the alcohol-water mixed solvent, and
- d2) isolating the precipitated 1-(6,7-dihydro-5H-benzo[6,7]cyclohepta[1,2-c]pyridazine-3-yl)-$N^3$-(7-(pyrrolidin-1-yl)-6,7,8,9-tetrahydro-5H-benzo[7]annulene-2-yl)-1H-1,2,4-triazole-3,5-diamine free base from the alcohol-water mixed solvent.

14. The process according to claim 13, wherein, during precipitation of the 1-(6,7-dihydro-5H-benzo[6,7]cyclohepta[1,2-c]pyridazine-3-yl)-$N^3$-(7-(pyrrolidin-1-yl)-6,7,8,9-tetrahydro-5H-benzo[7]annulene-2-yl)-1H-1,2,4-triazole-3,5-diamine free base in step (d1), the pH is increased further, as necessary, to maintain a pH at or above the level at which precipitation of 1-(6,7-dihydro-5H-benzo[6,7]cyclohepta[1,2-c]pyridazine-3-yl)-$N^3$-(7-(pyrrolidin-1-yl)-6,7,8,9-tetrahydro-5H-benzo[7]annulene-2-yl)-1H-1,2,4-triazole-3,5-diamine free base commences in step (d1).

15. The process according to claim 1, wherein the acid used in step (a) is selected from fumaric, citric and hydrochloric acid.

16. The process according to claim 1, wherein 146,7-dihydro-5H-benzo[6,7]cyclohepta[1,2-c]pyridazine-3-yl)-$N^3$-(7-(pyrrolidin-1-yl)-6,7,8,9-tetrahydro-5H-benzo[7]annulene-2-yl)-1H-1,2,4-triazole-3,5-diamine free base is 1-(6,7-dihydro-5H-benzo[6,7]cyclohepta[1,2-c]pyridazine-3-yl)-$N^3$-(7-(S)-(pyrrolidin-1-yl)-6,7,8,9-tetrahydro-5H-benzo[7]annulene-2-yl)-1H-1,2,4-triazole-3,5-diamine free base and is purified from a quantity of crude 1-(6,7-dihydro-5H-benzo[6,7]cyclohepta[1,2-c]pyridazine-3-yl)-$N^3$-(7-(S)-(pyrrolidin-1-yl)-6,7,8,9-tetrahydro-5H-benzo[7]annulene-2-yl)-1H-1,2,4-triazole-3,5-diamine.

17. The process according to claim 1, wherein the crude 1-(6,7-dihydro-5H-benzo[6,7]cyclohepta[1,2-c]pyridazine-3-yl)-$N^3$-(7-(pyrrolidin-1-yl)-6,7,8,9-tetrahydro-5H-benzo[7]annulene-2-yl)-1H-1,2,4-triazole-3,5-diamine is the product of a reaction between phenyl N'-cyano-N-(7-(pyrrolidin-1-yl)-6,7,8,9-tetrahydro-5H-benzo[7]annulen-2-yl)carbamimidate and 3-hydrazino-6,7-dihydro-5H-benzo[6,7]cyclohepta[1,2-c]pyridazine.

18. The process according to claim 17, wherein a starting solution of the crude 1-(6,7-dihydro-5H-benzo[6,7]cyclohepta[1,2-c]pyridazine-3-yl)-$N^3$-(7-(pyrrolidin-1-yl)-6,7,8,9-tetrahydro-5H-benzo[7]annulene-2-yl)-1H-1,2,4-triazole-3,5-diamine is brought into contact with the alcohol-water mixed solvent in step (a).

19. The process according to claim 18, wherein the starting solution of the crude 1-(6,7-dihydro-5H-benzo[6,7]cyclohepta[1,2-c]pyridazine-3-yl)-$N^3$-(7-(pyrrolidin-1-yl)-6,7,8,9-tetrahydro-5H-benzo[7]annulene-2-yl)-1H-1,2,4-triazole-3,5-diamine comprises a product solution resulting from the reaction between phenyl N'-cyano-N-(7-(pyrrolidin-1-yl)-6,7,8,9-tetrahydro-5H-benzo[7]annulen-2-yl)carbamimidate and 3-hydrazino-6,7-dihydro-5H-benzo[6,7]cyclohepta[1,2-c]pyridazine.

20. The process according to claim 18, wherein the starting solution employs a solvent other than the alcohol-water mixed solvent used in step (a).

21. The process according to claim 20, wherein the solvent of the starting solution is immiscible with the alcohol-water mixed solvent used in step (a).

22. The process according to claim 20, wherein the solvent of the starting solution is removed prior to step (b1).

23. A compound chosen from 1-(6,7-dihydro-5H-benzo[6,7]cyclohepta[1,2-c]pyridazine-3-yl)-$N^3$-(7-(pyrrolidin-1-yl)-6,7,8,9-tetrahydro-5H-benzo[7]annulene-2-yl)-1H-1,2,4-triazole-3,5-diamine free base, or 1-(6,7-dihydro-5H-benzo[6,7]cyclohepta[1,2-c]pyridazine-3-yl)-$N^3$-(7-(S)-(pyrrolidin-1-yl)-6,7,8,9-tetrahydro-5H-benzo[7]annulene-2-yl)-1H-1,2,4-triazole-3,5-diamine free base, obtained or obtainable by the process of claim 1.

24. The process according to claim 4, wherein the alcohol-water mixed solvent, prior to carrying out step (b1), is adjusted if necessary such that it contains approximately 75% alcohol by volume.

25. The process according to claim 6, wherein, in step (b1), the pH is increased to approximately 8.5.

* * * * *

UNITED STATES PATENT AND TRADEMARK OFFICE
CERTIFICATE OF CORRECTION

PATENT NO. : 9,994,553 B2  
APPLICATION NO. : 15/526220  
DATED : June 12, 2018  
INVENTOR(S) : Lene Raunkjaer Petersen Page 1 of 1

It is certified that error appears in the above-identified patent and that said Letters Patent is hereby corrected as shown below:

In the Claims

Column 13, Line 33, Claim 16: "146" should read --1-(6--.

Signed and Sealed this  
Twenty-eighth Day of August, 2018

Andrei Iancu  
*Director of the United States Patent and Trademark Office*